United States Patent [19]

West

[11] Patent Number: 4,915,097

[45] Date of Patent: Apr. 10, 1990

[54] JOINT SUPPORT DEVICE OF SHEEPSKIN TO INHIBIT MOVEMENT

[75] Inventor: Karen L. West, New South Wales, Australia

[73] Assignee: Victor L. West, New South Wales, Australia; a part interest

[21] Appl. No.: 195,565

[22] Filed: May 18, 1988

[51] Int. Cl.[4] .............................................. A61F 5/00
[52] U.S. Cl. .................................... 128/77; 128/80 G
[58] Field of Search .................... 128/77, 80 G, 87 A, 128/80 H

[56] References Cited

U.S. PATENT DOCUMENTS

| | | | |
|---|---|---|---|
| Re. 32,680 | 5/1988 | Pompa | 128/77 |
| D. 259,955 | 7/1981 | Helferich | 128/77 |
| 3,327,703 | 6/1967 | Gamm | 128/77 |
| 3,814,088 | 6/1974 | Raymond | 128/87 R |
| 4,013,070 | 3/1977 | Harroff | 128/77 |
| 4,471,770 | 9/1984 | Pompa | 128/77 |
| 4,716,892 | 1/1988 | Brunswick | 128/80 C |
| 4,765,319 | 8/1988 | Finnieston et al. | 120/77 |

FOREIGN PATENT DOCUMENTS 3622321 1/1988 Fed. Rep. of Germany ... 128/80 H

*Primary Examiner*—Edgar S. Burr
*Assistant Examiner*—Tonya Lamb
*Attorney, Agent, or Firm*—Jones, Tullar & Cooper

[57] ABSTRACT

A supportive cover to enclose a patient's joint such as a wrist, knee or elbow, the cover includes a sheet of sheepskin which is tightly wrapped around the user's joint with the fleece abutting the skin, with securing strips being provided to ensure that the sheet is wrapped tightly around the joint to inhibit without immobilizing movement thereof.

10 Claims, 2 Drawing Sheets

JOINT SUPPORT DEVICE OF SHEEPSKIN TO INHIBIT MOVEMENT

BACKGROUND OF THE INVENTION

This invention relates to support devices for parts of the human body and more particularly, but no exclusively to wrist support devices for sufferers of conditions such as rheumatoid arthritis. This condition is very painful and often crippling and has received considerably more publicity in recent times due to its association with the "computer age disease" known as "repetitive strain injury" or tenosynovovitis.

Medical theories on factors influencing the condition include hereditary genetics, diet, stress, work practices, and injuries.

Sufferers claim that pain most often develops during periods of inactivity, thought to be the result of limited blood circulation created by stagnation of the white cells. This occurs particularly in the joints of the body where tissue is relatively tin.

Flexing movement of an unsupported wrist while asleep can also create considerable discomfort.

Devices offered to alleviate the condition include sheaths and braces which may surround a limb member or joint and may include ribs or stays to limit flexing movement.

They are generally made of leather, plastic materials, canvas or elastic bandage. They are often cumbersome to apply and/or remove, and uncomfortable to wear due to poor heat and vapour dissipation, and create chaffing due to friction.

There are available sheep skin pads or "socks" which are adapted to maintain the heat within a patient's joint. However these previously known sheep skin products do not act as a protector for the joint and generally allow free movement thereof.

SUMMARY OF THE INVENTION

It is the object of the present invention to overcome or substantially ameliorate the above disadvantages.

There is disclosed herein a supportive cover to enclose a patient's joint, said cover comprising a sheet of sheep skin having a fleece layer backed by a skin layer, said sheet having opposite edges which are brought together about the joint so as to encompass the joint, securing means attached to the skin portion to tightly secure the sheet in a wrapped position with the fleece layer adjacent the skin of the patient, and wherein said securing means holds adjacent portions of opposing edges together thereby inhibiting movement of the joint.

BRIEF DESCRIPTION OF THE DRAWINGS

A preferred form of the present invention will now be described by way of example with reference to the accompanying drawings, wherein.

DESCRIPTION OF PREFERRED EMBODIMENTS

Figure 1:
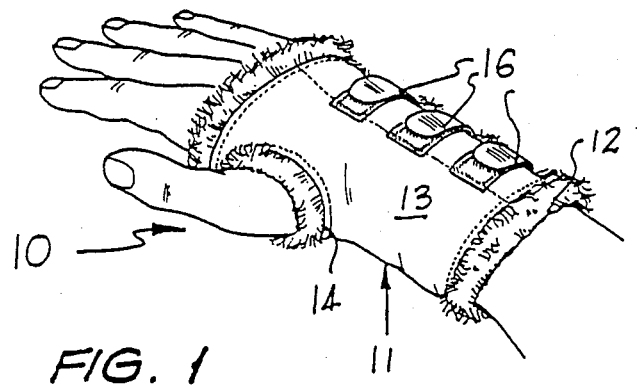
FIG. 1 is a schematic perspective view of a sheep skin wrist support applied to a patient's wrist.
Figure 2:
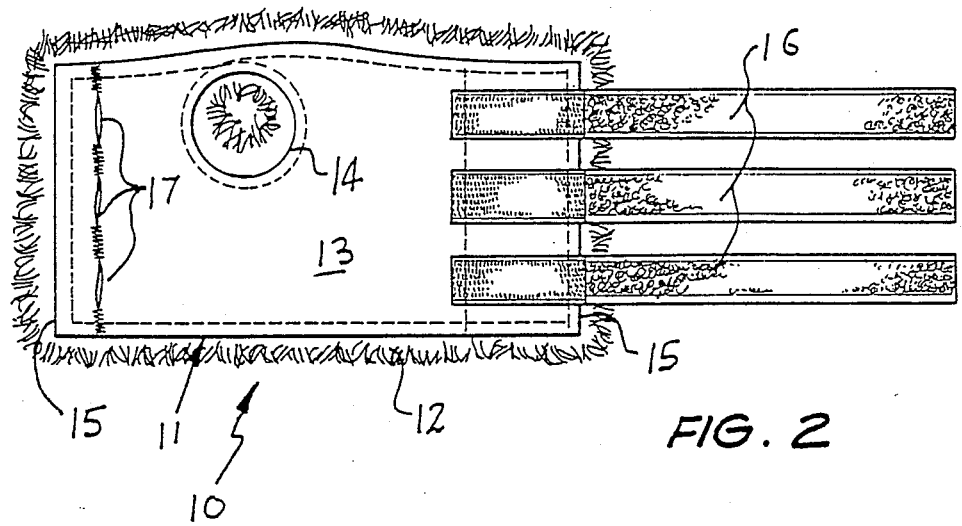
FIG. 2 is a schematic plan view of the support of FIG. 1.
Figure 3:
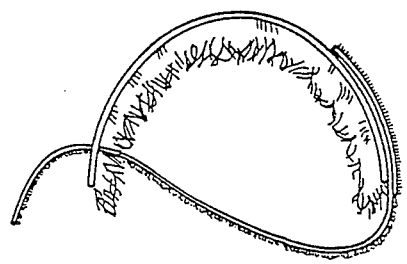
FIG. 3 is a schematic end elevation of the support of FIG. 1 in a partly wrapped configuration.
Figure 4:
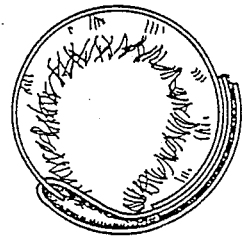
FIG. 4 is a schematic end elevation of the support of FIG. 1 in a fully wrapped configuration.

In FIGS. 1 to 4 there is schematically depicted a sheep skin support 10 adapted to be applied to the wrist of a user. The support 10 consists of a sheet 11 of sheep skin consisting of a fleece layer 12 and a skin backing layer 13. The sheet 11 is provided with an aperture 14 through which the user's thumb may pass. The sheet 11 is further provided with opposite edges 15 which are bought together so that the sheet 13 tightly wraps around the wrist.

Secured to the skin layer 15 are VELCRO (registered Trade Mark) hook and loop type fastener strips 16 having, for example, hook portions 16' and loop portion 16". The strips pass through apertures 17, to be folded back upon themselves to retain the sheet 11 in the tightly wrapped position. In doing so, the edges 15 are held together thereby inhibiting movement of the joint.

Figure 5:
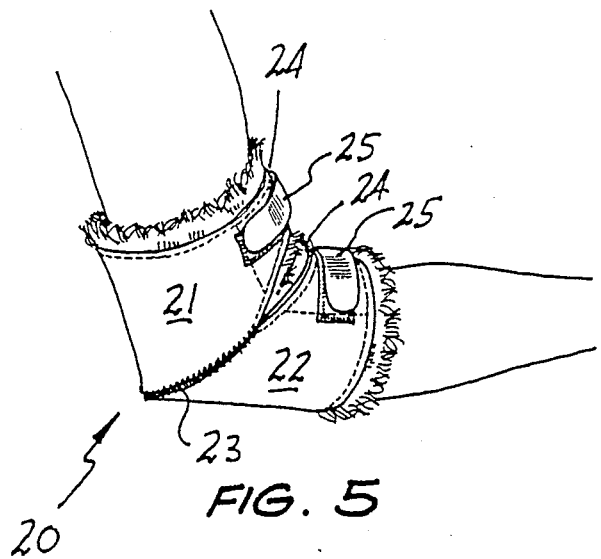
FIG. 5 is a schematic perspective view of a sheep skin elbow support applied to a patient's elbow.

In FIG. 5 an elbow support 20 is illustrated. The elbow support 20 includes two sheets 21 and 22 of sheep skin secured by means of a seam 23 so as to be of a generally "L-shaped" configuration. Each sheet 21 and 22 has a pair of opposite edges 24 which are held closely together by means of securing strips 25 in a similar manner to that discussed with reference in FIGS. 1 to 4. In this particular embodiment, due to the configuration of the support 20, when the strips 25 are firmly placed in position, the support 20 inhibits movement of the elbow joint.

Figure 6:
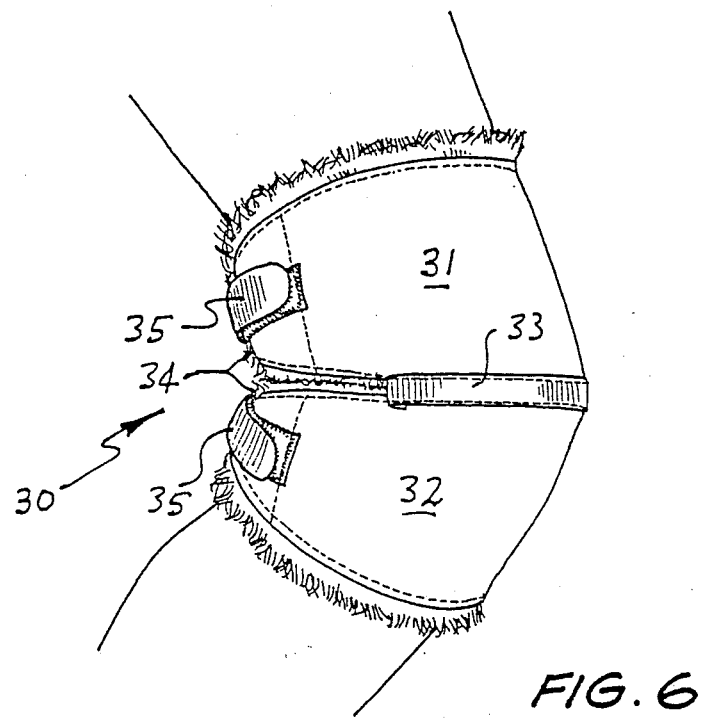
FIG. 6 is a schematic perspective view of a sheep skin knee support applied to the knee of a patient.

In FIG. 6 a knee support 30 is schematically depicted. The knee support 30, in a similar member to the elbow support of FIG. 5, is provided with a pair of sheep skin sheets 31 and 32 secured together by means of a seam 33. Each sheet 31 or 32 has pairs of opposite edges 43 which are securely held adjacent to each other by means of securing tabs 35 in a similar manner to that discussed with reference to FIGS. 1 to 4.

Due to the generally "L-shaped" configuration of the support 30, when the tab 35 are securely placed in position, the support 30 inhibits movement of the joint.

As can be seen from the above discussed preferred embodiments of the present invention, the securing means (strips 16 and tabs 25 and 35) are attached to the skin portion of the sheep skin, and are adapted to place the fleece layer 12 adjacent the skin of the user.

When the wearer is in a rest position such as when trying to sleep at night the above discussed supports maintain warmth in the thinly fleshed areas of the wrist/hand, knee or elbow thereby assisting circulation. Due to the absorbent nature of wool fibre the support is comfortable to wear even during hot or humid conditions.

The depth of the fleece above the surface of the leather skin is not critical providing it is at least approximately 5 mm, but is generally in the range 5–15 mm which range permits relatively firm pressure to be applied without restricting blood circulation.

The resiliency of the lamb's wood skin together with the circumferential tension provides longitudinal and torsional support.

Wearers of the support devices suffer less pain and experience less swelling of the supported joints than previously obtained by the use of other support devices.

Confirmation of its effectiveness was shown by a rheumatoid arthritis sufferer wearing the support on one wrist while sleeping and leaving the other unprotected.

On waking the unprotected wrist was swollen and painful taking at least two hours before the person could in any way use the hand without feeling stressed or uncomfortable in doing so, whilst the supported/protected hand was not painful or swollen and was useable immediately.

The same result was achieved regardless of which wrist was supported overnight.

The use of lamb's wool skin for the support device achieves the objectives of durability, launderability and non-chaffing to the wearer's skin.

Still further, the sheep skin, when tightly wrapped around the joint, inhibits movement of the joint. This has the advantage of restricting unrestrained movement during sleep.

The foregoing describes only some embodiments of the present invention and modifications, obvious to those skilled in the art, can be made thereto without departing from the scope of the present invention.

What I claim is:

1. A supportive cover to enclose a patient's wrist joint, knee joint or elbow joint, said cover including means to inhibit movement of the joint without immobilizing the joint, said means consisting of a sheet of sheep skin having a resilient fleece layer between 5 and 15 mm thick and backed by a skin layer, said sheet having opposite edges which are brought together about the joint so as to encompass the joint, securing means attached to the skin portion to tightly secure the sheet in a wrapped position to produce a circumferential tension about the joint with the fleece layer adjacent the skin of the patient, said securing means holding adjacent portions of opposing edges together to apply firm pressure to inhibit without immobilizing movement of the joint without restricting the patient's blood circulation, the fleece having a resiliency which cooperates with said circumferential tension to provide longitudinal and torsional support for the joint.

2. The supportive cover of claim 1, wherein the support is a wrist support, wherein said sheet is provided with an aperture through which a user's thumb is to pass, and wherein said opposing edges run generally longitudinally of the user's arm.

3. The supportive cover of claim 2, wherein said securing means include a plurality of securing strips located at spaced intervals along said edges, which strips extend from one edge, to pass through apertures adjacent the other edge whereat the strips are bent back upon themselves to enable tightening of the sheet about the wrist joint.

4. The supportive cover of claim 1, wherein the support is a knee or elbow support, and said cover includes a pair of said sheets of sheep skin, joined by a seam so that the cover has a generally "L-shaped" configuration, with each sheet having a pair of opposite edges which in use are held together by said securing means.

5. The supportive cover of claim 4 wherein said securing means includes a securing tab for each pair of opposite edges, which securing tab extends from one edge, through an aperture adjacent the other edge and is folded back upon itself to secure the two edges together.

6. A supportive cover to enclose and inhibit the motion of a patient's joint,
including means to inhibit movement of the joint without immobilizing the joint, said means consisting of;
a sheet of sheep skin having a resilient fleece layer backed by a skin layer, said sheet being shaped to encompass a patient's joint and having at least first and second opposite edges which are brought together when the sheet encompasses a joint;
a plurality of securing strips located at spaced intervals along said first edge;
a plurality of apertures formed in said sheet along said second edge, said apertures being aligned with corresponding ones of said strips; and
fastener means on each of said strips for fastening each said strip when said strip passes through a corresponding aperture and is folded back on itself to secure the sheet in a wrapped position to produce a circumferential tension about the joint with the fleece layer adjacent the skin of the patient and the sheet encompassing the joint with said edges adjacent each other to maintain warmth in the patient's joint, said strips passing through said apertures to pull said first and second edges together sufficiently tightly to cause said sheet o inhibit without immobilizing motion of a patient's joint without restricting the patient's blood circulation, the fleece having sufficient resiliency to permit limited motion of the joint while cooperating with said circumferential tension to provide longitudinal and torsional support for the joint, said fastener means securing said strips and holding adjacent portions of said first and second edges together.

7. The supportive cover of claim 6, wherein said sheet is shaped to fit the wrist of a patient, said sheet including an aperture through which a patient's thumb may pass, said sheet being elongated to extend generally longitudinally of a patient's arm, said first and second edges extending longitudinally along said sheet.

8. The supportive cover of claim 6, further including a second sheet of sheep skin having a fleece layer and a skin layer, having at least third and fourth opposite edges which are brought together when said second sheet encompasses a patient's joint, having a second plurality of securing strips located at spaced intervals along said third edge, having a plurality of apertures formed in said sheet along said fourth edge, said apertures being aligned with corresponding ones of said second plurality of strips, and fastener means on each of said second plurality of strips for fastening each said strip when it passes through a corresponding aperture and is folded back on itself; and
seam means joining said first and second sheets to form an elongated cover having an L-shaped configuration with said first and second edges and said third and fourth edges extending longitudinally along the L-shaped cover, the first and second together sufficiently tightly to cause said sheets to inhibit motion of a patient's joint.

9. The supportive cover of claim 6, wherein said fleece layer has a thickness of at least about 5 mm.

10. The supportive cover of claim 6, wherein said fleece layer has a thickness of between about 5 mm and 15 mm.

* * * * *

UNITED STATES PATENT AND TRADEMARK OFFICE
CERTIFICATE OF CORRECTION

PATENT NO.   :   4,915,097
DATED        :   April 10, 1990
INVENTOR(S)  :   KAREN L. WEST It is certified that error appears in the above-identified patent and that said Letters Patent is hereby corrected as shown below:

Column 4, Claim 6, line 26, "sheet o inhibit"

should read --sheet to inhibit--.

Column 4, Claim 8, lines 58-59, a line of text is missing and should be inserted between the lines thus:

--plurality of strips pulling corresponding edges of said sheets--.

Signed and Sealed this

Second Day of July, 1991

Attest:

HARRY F. MANBECK, JR.

Attesting Officer

Commissioner of Patents and Trademarks